(12) United States Patent
Fresco

(10) Patent No.: US 6,976,959 B2
(45) Date of Patent: Dec. 20, 2005

(54) DUAL TONOMETER

(76) Inventor: Bernard B. Fresco, 40 St. Clair Avenue East, Suite 303, Toronto, Ontario (CA) M4T 1M9

( * ) Notice: Subject to any disclaimer, the term of this patent is extended or adjusted under 35 U.S.C. 154(b) by 0 days.

(21) Appl. No.: 10/764,447

(22) Filed: Jan. 27, 2004

(65) Prior Publication Data

US 2004/0186367 A1   Sep. 23, 2004

Related U.S. Application Data

(63) Continuation of application No. 09/852,691, filed on May 11, 2001, now Pat. No. 6,706,001.

(51) Int. Cl.$^7$ ................................................ A61B 3/16
(52) U.S. Cl. ..................... 600/398; 600/399; 600/405; 73/157
(58) Field of Search ............................... 600/398, 399, 600/405, 403, 406, 561, 587; 73/157, 80

(56) References Cited

U.S. PATENT DOCUMENTS

| | | |
|---|---|---|
| 1,637,421 A | 8/1927 | Lipschutz |
| 1,661,718 A | 3/1928 | Davis |
| 2,656,715 A | 10/1953 | Tolman |
| 2,882,891 A | 4/1959 | Husted |
| 2,984,099 A | 5/1961 | Tolman |
| 3,287,957 A | 11/1966 | Martens |
| 3,677,074 A | 7/1972 | Murr |
| 3,992,926 A | 11/1976 | Berryhill |
| 4,505,278 A | 3/1985 | Alban |
| 4,886,066 A | 12/1989 | Ingalz et al. |
| 5,174,292 A | 12/1992 | Kursar |
| 5,176,139 A | 1/1993 | Fedorov et al. |
| 5,197,473 A | 3/1993 | Fedorov et al. |
| 5,251,627 A * | 10/1993 | Morris ................. 600/398 |
| 5,349,955 A | 9/1994 | Suzuki |
| 5,830,139 A * | 11/1998 | Abreu ................. 600/405 |
| 6,143,011 A | 11/2000 | Hood et al. |
| 6,251,071 B1 | 6/2001 | Fresco et al. |
| 6,524,243 B1 * | 2/2003 | Fresco ................. 600/399 |

FOREIGN PATENT DOCUMENTS

| | | |
|---|---|---|
| DE | 34 21 701 A | 12/1984 |
| EP | 0 584 929 | 2/1994 |
| FR | 2 542 603 | 3/1983 |
| RU | 2004187 | 12/1993 |
| SU | 0457466 | 1/1975 |
| WO | WO97/43946 | 11/1997 |

OTHER PUBLICATIONS

Adler's Physiology of the Eye, pp. 257-273.
Physiology of the Eye, Chapter 3, pp. 31-76.

* cited by examiner

Primary Examiner—Theresa Trieu
(74) Attorney, Agent, or Firm—Bereskin & Parr

(57) ABSTRACT

An applanation tonometry system, for measuring pressure within an eye, the tonometry system comprising: an applanation tonometer device for providing specific applanation pressure to a plurality of locations on an eye; an electrical process controller for measuring pressure within the eye; and a tonometer hands free holder adapted to secure the tonometer device over the eye whilst measuring the pressure within the eye.

6 Claims, 6 Drawing Sheets

DUAL TONOMETER

FIELD OF THE INVENTION

This invention relates to an apparatus for and a method of measuring intraocular pressure in the human eye. This invention more particularly relates to an applanation tonometer system for measuring pressure and diurnal pressure variations within the eye.

BACKGROUND OF THE INVENTION

It is well known that excessive internal pressure within the human eyeball is a component of glaucoma, a disease of the eye. This disease accounts for a significant percentage of all blindness. Surveys have shown it to be present and unrecognized in a significant number of people, particularly people over the age of 40 and even more so for people over the age 50.

It is also known that where the presence of glaucoma can be identified at an early stage, damage to the eye and subsequent blindness can be arrested. Appropriate medication and surgery can serve to arrest the progress of the disease so that useful vision is retained.

In view of the fact that glaucoma is widespread, numerous proposals have been made for measuring the internal eyeball pressure. Many of these are complex precision instruments, which are expensive, and which require elaborate clinical settings for their operation. Typically, such instruments apply an amount of force to the eyeball, sufficient to allow an objective measurement of specific flattening (applanation) or indenting (indentation) of the surface of the eye. The amount of force required to achieve a certain applanation or indentation is correlated with the intraocular pressure measured internally, and usually expressed in mm of mercury.

Conventionally, the clinical instrument involved has some element which is applied directly to the cornea of the open eye to measure the applanation or indentation of the cornea. In view of natural human reflexes, this requires a topical anesthetic. The equipment is complex and costly and requires a trained and sophisticated technician to operate it. Other proposals have been made, and the following patents list proposals known to the applicant: U.S. Pat. Nos. 1,637,421; 1,661,718; 2,656,715; 5,176,139; and 5,197,473; French Patent 2,542,603; and Russian Federation Patents 2,004,187 and 457,466.

The Lipschutz U.S. Pat. No. 1,637,421 is a pressure indicator. It is not concerned with measuring eyeball pressure, but rather it is concerned with applying pressure to other parts of the human body. It is based on the well known phenomenon that sensitivity to pressure of an area of the body is an indication of disease. More particularly, it relies on the fact that the progress of the disease is related to the sensitivity of an associated area of the body. As such, it provides a device enabling the pressure applied to a particular area to be measured, so this pressure can be correlated with the progress of the disease. No clear directions are given, with regard to applying this technique to the human eye. Measuring pressure in the human eye presents unique and difficult problems, as compared to other parts of the anatomy. As the human eye is sensitive and delicate, everyone has a strong, natural reflex to close their eyes, if any attempt is made to touch the eye. This Lipschutz patent does not address this issue.

A hardness testing device is disclosed in U.S. Pat. No. 1,661,718 which is of marginal relevance.

An ocular tension indicator is disclosed in the Tolman U.S. Pat. No. 2,656,715. However, this requires the eyeball to be contacted. It relies upon relative axial displacement of different components of known, set weight, to determine the pressure within the eye. As such, it appears to be a delicate, precision instrument. Since it must contact the naked eye, it cannot be used outside of a clinical setting.

The two Fedorov U.S. Pat. Nos. 5,176,139 and 5,197,473 disclose an ocular tonometer and a related method. This relies on a somewhat unique technique where a ball is permitted to fall freely onto an eyelid-covered cornea. The kinetic energy of the ball deforms a cornea. The amount of the ball rebound varies depending upon the amount of intraocular pressure and this is judged against the height of the ball rebound. This technique would appear difficult to carry out, since it depends upon judging the height of the ball rebound.

Russian Patent 457,466 discloses an intraocular pressure transducer. This relies upon a Hall effect generator. Weights determine the penetration force of a plunger, whose displacement is sensed by the Hall effect generator with an output proportional to the displacement. Russian Patent 2,004,187 discloses an eye tonometer having a hollow cylindrical body with tips and working end face surfaces. It is not clear how this device is intended to work. In any event, it is again intended to be applied to the naked eyeball, which again would require the application of a topical anesthetic in a clinical setting.

U.S. Pat. No. 3,992,926 discloses an applanation tonometer incorporating a transducer for generating a digital readout of pressure. In use, the tonometer device measures differential pressure changes during the intraocular pressure measurement process. The transducer identifies a specific pressure change which corresponds with known tonograph results.

PCT patent application PCT/CA97/00341 discloses an applanation tonometer for measuring intraocular pressure within the eye. The tonometer includes a main body and a plunger, wherein the plunger is brought up against the eyelid of a closed eye and the main body is pushed towards the eyelid, which displaces the plunger into the main body. Displacement of the plunger relative to the main body is terminated when a pressure phosphene is detected. The displacement of the plunger is determined by a marker which is also indicative of the intraocular pressure within the eye.

Now, one of the problems with measuring intraocular pressure is that it can vary during the course of the day, and even from hour to hour. Accordingly, it is highly desirable to provide some simple technique for measuring this pressure. This technique should enable an ordinary person to measure the intraocular pressure within their eyes, without requiring complex expensive equipment, without requiring attendance at a clinic or the like, and without requiring the time of highly trained clinical staff. Also, it is highly desirable to record diurnal (occurring in a 24-hour period) variations in intraocular pressure overnight. It has been found that glaucoma patients have much higher diurnal intraocular pressure variations (8–11 mm Hg) in comparison to healthy subjects (about 4 mm Hg variations).

SUMMARY OF THE INVENTION

In an applanation tonometry system for measuring pressure within an eye, the system comprising: an applanation tonometer device for providing specific applanation pressure to a plurality of locations on an eye; an electrical process controller for measuring pressure within the eye; and a tonometer hands free holder adapted to secure the tonometer device over the eye. The tonometer device further comprises: a main body having first and second end portion; a plurality of plunger members slidably mounted in the main body, each of the plurality of plunger members having a first and second end, the second end comprising a contact member protruding from the first end portion of the main body, and a second end mounted within the main body, in use, each contact member applies a specific applanation pressure to a specific location on the eye; and a plurality of transducer devices mounted within the main body, for converting the specific applanation pressure of each contact member to an electrical signal.

In accordance with another aspect of the present invention, a method of obtaining pressure within the eyeball of a subject comprises the steps of applying a constant known reference pressure to a first location on the eyelid of the subject; applying at least a second pressure to an at least second location on the eyelid of the subject; increasing the at least second pressure until an increase in the constant known reference pressure is detected; and terminating the increasing of the at least second pressure, when the increase in the constant known reference pressure is detected.

The method of obtaining pressure within the eyeball of a subject includes providing a tonometer device comprising: a main body; a first and second plunger member slidably mounted in the main body, the first and second plunger member having a first end comprising a first and a second contact member respectively and having a second end mounted within the main body, the second end of the first and second plunger member in contact with a first and second transducer device respectively, whereby the first transducer device detects displacement of the first plunger member and the second transducer device detects displacement of the second plunger member, the method comprising:
(a) adjusting movement of the first plunger and the second plunger, so the first plunger is in light contact with the first location on the eyelid, and the second contact member is in light contact with the second location on the eyelid;
(b) actuating the first plunger member so as to apply a constant known applanation pressure to the first location on the eyelid;
(c) actuating the second plunger member so as to apply an increasing second applanation pressure to the second location on the eyelid; and
(d) terminating the actuating movement of the second plunger member, when the first transducer device detects an increase in the constant known applanation pressure.

DETAILED DESCRIPTION OF THE DRAWINGS

For a better understanding of the present invention and to show more clearly how it may be carried into effect, reference will now be made, by way of example, to the accompanying drawings, which show preferred embodiments of an applanation tonometry system of the present invention, and in which.

DETAILED DESCRIPTION OF THE PREFERRED EMBODIMENT

Figure 1:
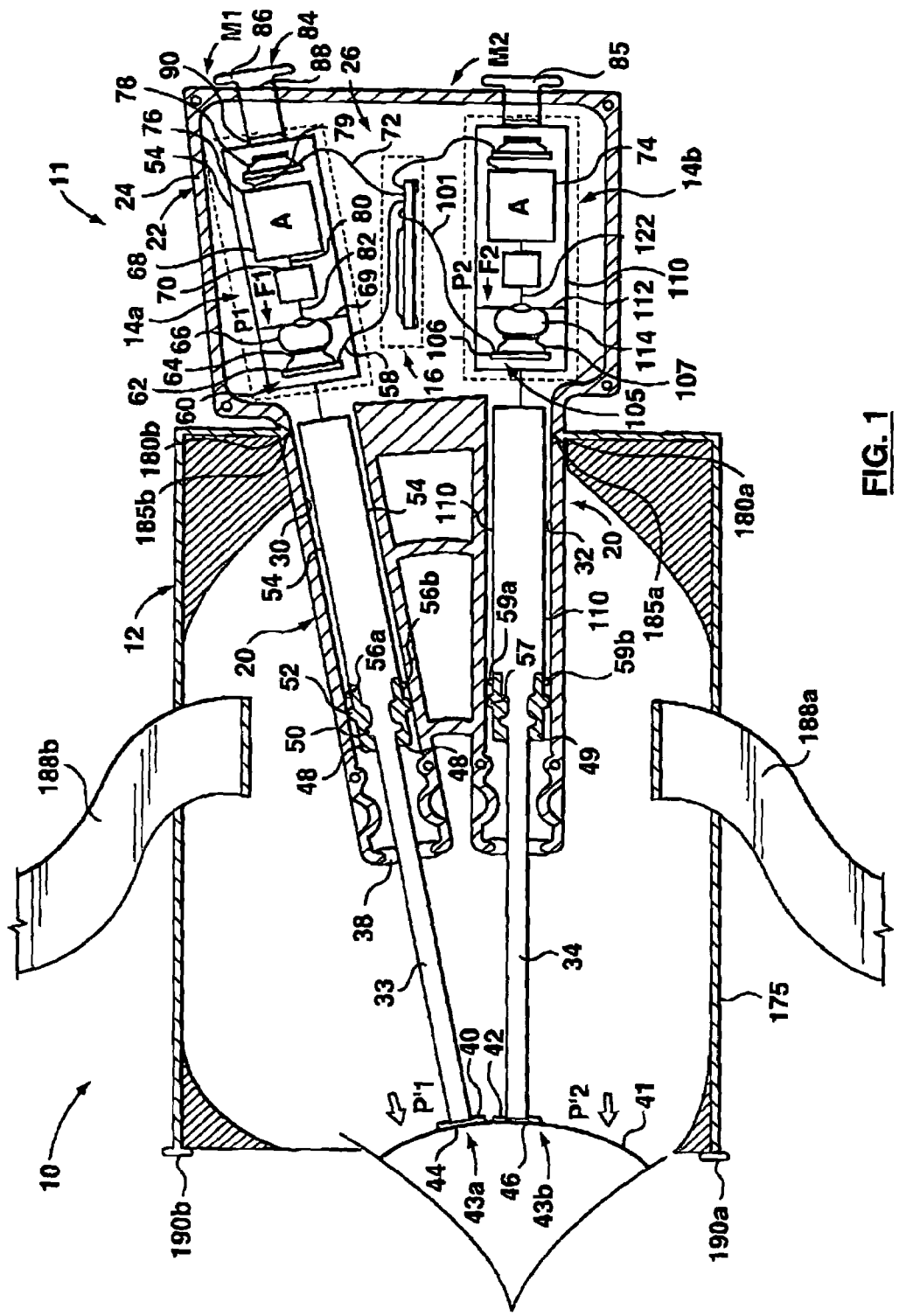
FIG. 1 illustrates a vertical cross sectional view of a first embodiment of an applanation tonometry system incorporating.

FIG. 1 illustrates a cross sectional view of an applanation tonometry system 10 comprising a tonometer hands free holder 12, an applanation tonometer device 11, first and second transducer devices 14a, 14b, and an electrical process controller 16. The tonometer device 11 has a main body 20, wherein the main body 20 has a first and second hand portion.

The first portion of the main body 20, as shown in the drawing, includes a housing 22 of increased cross section, where the cross section can be either rectangular or circular. The housing 22 comprises an outer casing 24 and a housing cavity 26 for holding the first and second transducer devices 14a, 14b and the electrical process controller 16.

The second portion of the main body 20 defines first and second internal bores 30, 32 extending, in use, from the housing cavity 26 towards the eye (as detailed below). The cross section of each internal bore 30, 32 is generally circular and is such that a respective first or second plunger member 33, 34 is free to move axially therein.

The first plunger member 33 extends out of the second end of the main body 20 and is supported for sliding movement relative to the main body 20 and within the bore 30. The sliding movement of the plunger 33 within the bore 30 is achieved by means of a bearing 38, located at the second end of the main body 20.

The left hand end portion of the first plunger 33 includes a first head or contact member 40, which can be any desired shape. As illustrated in FIG. 1, the first contact member 40 is preferred to present a flat, circular disk surface, as indicated by 44, i.e. as a conventional applanation tonometer. Otherwise, the profile to the right of the disk surface, is not critical.

It is also to be noted that in contrast to conventional applanation tonometers intended for application directly to the eyeball, the head or contact member is intended for application to the eyelid (although application directly to the eyeball is encompassed by the present invention). Accordingly, a larger applanation disk 44 may be required. The right hand end of the first plunger 33 is attached to a second bearing member 48, which includes an annular channel 50 for receiving and retaining the right hand end of the first plunger 33. The bearing member 48 further comprises an annular second bearing member, indicated at 52. The length of the plunger extending between the first contact member 40 and right hand end of the plunger is of uniform cross section and hollow. The first bearing member 38 and the second bearing member 52, provide axial support for the first plunger 33 and allow the first plunger 33 to move within the first bore 30 with reduced frictional force. This ensures that the frictional force between the plunger 33 and bore 30 is negligible so that any load applied to contact member 40 is transmitted through the first plunger 33 to the transducer device 14a.

A first elongate frame member 54 is attached at one end to the second bearing member 48 by means of a pair of securing members 56a, 56b. The other end of the elongate frame member 54 extends axially along the first bore 30 and into the housing cavity 26 which holds the transducer devices 14a, 14b and the electrical process controller 16. Thus, the contact member 40, the plunger 33, the bearing member 48 and the elongate frame member 54 are integral and move as a unit within the bore 30 and housing cavity 26. In use, pressure, as indicated by P1, is applied to the right hand end of the elongate fram member 54 in the direction of arrow F1. This causes an outward displacement of the elongate frame member 54 and first plunger 33 relative to the main body 20. The outward displacement of the first plunger 33 in turn transfers the pressure, indicated by P1, to the outer surface of an eyelid, as indicated at 43a, by means of first contact member 40. Thus, it will be appreciated that in accordance with the present invention, the first plunger member 33, the first elongate member 54 and first transducer device 14a define a first pressure applicator for applying applanation pressure.

Similarly, a second elongate frame member 110 is attached at one end to a third bearing member 49 by means of a pair of securing members 59a, 59b. The other end of the second elongate frame member 110 extends axially along the second bore 32 and into the housing cavity 26. The second plunger 34 is also connected to the third bearing member 49. Identical to the first plunger member 33, the left hand end portion of the second plunger 34 (as viewed in FIG. 1) includes a second head or contact member 46, which can be any desired shape. The plunger 33, the third bearing member 49 and the second elongate frame member 110 are integral and move as a unit within the second bore 32 and housing cavity 26. In use, pressure, as indicated by P2, is applied to the right hand end of the elongate frame member 110 in the direction of arrow F2. This causes an outward displacement of the second elongate frame member 110 and second plunger 34 relative to the main body 20. The outward displacement of the second plunger 34 in turn transfers the pressure, indicated by P2, to a second surface on the eyelid, as indicated by 43b, by means of the second contact member 46. Thus, it will be appreciated that the second plunger member 34, the second transducer device 14b and second elongate member 110 define a second pressure applicator for applying applanation pressure.

Both the first and second pressure applicator are comprised of substantially identical components and therefore, only the first pressure applicator will be described in detail. Accordingly, the description for the first pressure applicator also applies to the second pressure applicator. In accordance with the scope of the present invention, at least two pressure applicators apply applanation pressure to two separate locations on the eyelid.

The electrical process controller 16 within the housing cavity 26 is responsible for controlling the actuation of actuator devices 68 and 74. Actuators 68 and 74 generate the outward displacement of the first and second plungers 33, 34, respectively, which provide applanation pressure to the surface of the eyelid 41. The electrical process controller 16 monitors and controls the magnitude of applied pressure applied to the various locations on the eyelid 41, by means of the first and second transducer devices 14a, 14b. Furthermore, the electrical process controller 16 processes electrical signals received from both the first and second transducer devices 14a, 14b in order to determine the pressure within a subject's eye.

The pressure applied by the first plunger 33 to the eyelid 41 is both measured and generated by the first transducer device 14a. The first transducer device 14a comprises a first sensing device 60, a first analog-to-digital convertor (not shown in FIG. 1), a first actuator device 68 and a first coupling interface device 70. The first sensing device 60 has a sensor input and output, wherein the sensor input receives the pressure magnitude applied by the first plunger 33 to the eyelid 41. Based on the pressure magnitude received by the sensor input, the sensing device 60 generates an electrical pressure signal at the sensor output, which is in proportion to the pressure magnitude. The analog to digital converter receives the electrical pressure signal from the sensing device 60 and generates a digitized pressure signal. The electrical process controller 16 processes the received digitized pressure signal generated by the analog to digital convertor. Based on this processed digitized pressure signal, the electrical process controller 16 sends a first digital control signal to the actuator device 68 by means of conductor 72. Once the first actuator device 68 receives the first digital control signal, it actuates the plunger 33 in order to provide a specific or pre-determined applanation pressure to the eyelid 41. As illustrated in FIG. 1, it is the linear displacement of the plunger 33 relative to the main body 20, which causes applanation pressure to the eyelid 41. The displacement of the plunger 33 is converted to a pressure magnitude by the sensing device 60, whereby the pressure magnitude is correlated with a pre-determined pressure value corresponding to the linear displacement of the plunger 33. As the applanation pressure applied by the plunger reaches the desired level, the digital control signal terminates the movement of the plunger 33. Consequently, the sensing device 60 and electrical process controller 16 are implemented to form a closed-loop feedback control system whereby, the position of the plunger 33 is controlled based on a pre-determined target pressure.

It will be appreciated that the analog to digital conversion may not be required, especially if the electrical process controller 16 is capable of receiving analog electrical signals directly from the sensing device 60. This would be the case if the electrical process controller was implemented as a custom designed mixed signal (analog and digital) IC chip. In applications where, for example, the process controller is implemented using a standard off-the-shelf FPGA (Field Programmable Gate Arrary) device (with only digital inputs), the all digital inputs of the FPGA would require analog signals to be converted to digital format prior to being received, as described in the previous paragraph.

The first actuator device 68 includes a first servo motor device 76 having a rotatable shaft member 80 and an electrical motor controller device 78. The motor controller device 78 drives and controls the rotation movement of the motor device's shaft 80 based on the digitized control signal received from the electrical process controller 16. Similarly, the second actuator device 74 is identical in structural components to that of the first actuator device 68.

The first actuator device 68 is implemented using a servo-motor configuration. Therefore, the electrical motor controller device 78 receives the digital control signal directly from the electrical process controller device 16 by means of conductor 72. The motor controller device 78 receives the digital control signal and generates a Pulse Width Modulated Signal (PWM), which is sent by conductor 79 to the servo motor device 76. The PWM signal is a pulse train having a fixed period (e.g. 20 ms) and variable pulse width (e.g. 1–2 ms), which is used to drive the servo motor device 76. Based on the digitized control signal (e.g. 8-bit binary code corresponding to values between 0–255) received by the motor controller 78, the motor controller 78 generates a PWM signal of specific pulse width value capable of varying the angular position of the rotatable shaft 80 between 0–180 degrees. The angular position of the shaft member 80 is normally initialized to a mid-range position of 90 degrees by applying a 1.5 ms PWM signal to the motor device 76. By varying the PWM signal between 1.5 ms and 1 ms, the shaft 80 of motor device 76 will rotate between 90 and 0 degrees (anti-clockwise motion). Similarly, by varying the PWM signal between 1.5 ms and 2 ms, the shaft 80 of motor device 76 will rotate between 90 and 180 degrees (clockwise motion). Consequently, the motor controller can incrementally vary the angular position of the shaft member 80 over a range of 90 degrees in either direction (clockwise and anti-clockwise), where each incremental degree of rotation can be in the region of less than a degree.

The coupling interface includes a coupling input for receiving the rotatable shaft member 80 of servo motor 76, and a coupling output having a contact rod 82 adapted to engage the sensing device 60. The coupling interface device 70 couples the angular rotation of the shaft 80 received by the coupling input into linear motion (forwards or backwards) of the contact rod 82 at the coupling output (e.g. by use of a screw mechanism). The contact rod 82 engages a first pressure applanation plate 69, wherein the pressure applanation plate 69 is an integral part of the elongate frame member 54. Therefore, as the shaft 80 rotates, the linear motion of the contact rod 82 axially displaces the pressure applanation plate 69, the elongate frame member 54 and consequently the first plunger member 33.

Figure 2:
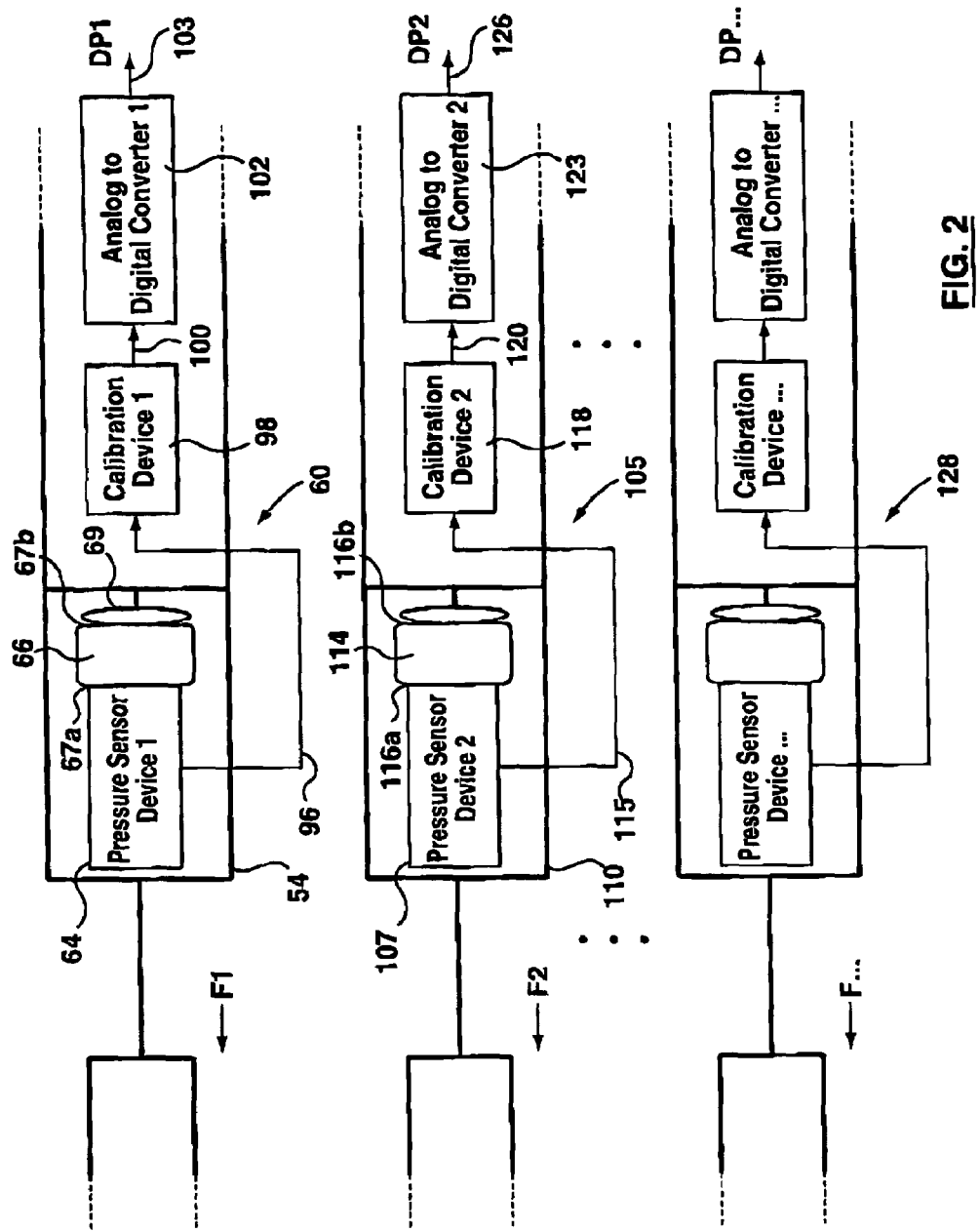
FIG. 2 illustrates a schematic view of the embodiment of each of the transducer devices within the applanation tonometry system of FIG. 1.

Referring to FIGS. 1 and 2, the sensing device 60 comprises a first pressure sensor IC device 64 and a first elastomer interface member 66 having first and second opposing surfaces, as defined by 67a and 67b, respectively (see FIG. 2). The pressure sensor IC device 64 incudes a pressure sensing surface and an electrical sensor output 96 (FIG. 2). The first surface 67a of the elastomer member 66 is in contact with the pressure sensing surface of the pressure sensor device 64. The pressure applanation plate 69, which forms part of the elongate frame member 54, is in contact with the second surface 67b of the elastomer interface member 66. As the actuator device 68 displaces the contact rod 82, the pressure applicator plate 69 and the elongate frame member 54 outwards, as indicated by arrow F1, the pressure applicator plate 69 applies a specific displacement to the surface 67b of the elastomer interface member 66. This displacement generates a corresponding pressure within the elastomer interface 66 which in turn is applied to the first surface 67a. As the elastomer interface 66 is compressed against the surface of the pressure sensor IC 64, the sensor output of the pressure IC 64 generates a corresponding electrical pressure signal in proportion to the applied pressure.

Referring to FIG. 1, it is to be understood that in an alternative embodiment of the present invention, the first pressure applicator plate 69 is not attached to the elongate frame member 54 and only contacts the first surface 67b (see FIG. 2) of the elastomer member 66. Also, the first sensing device circuit board 62, which includes the pressure sensor IC device 64 is then attached to the elongate frame member 54. As the actuator device 68 displaces the contact rod 82, the pressure applicator plate 69 (which is now not an integral part of the elongate frame member) applies pressure to the elastomer member 66. This in turn displaces the elastomer member, sensing device circuit board 62, elongate frame member 54 and plunger 33 outward towards the eyelid 41. As pressure is applied to the eyelid 41 by the first contact member 40, the elastomer member 66 is compressed between the pressure sensor IC device 64 (resisting the outward movement) and the actuated pressure applicator plate 69 (moving outward). In this embodiment, the pressure signal generated as a result of the elastomer member 66 compressed against the pressure sensor IC device 64 is directly correlated with applanation pressure applied to the eyelid 41 by the first contact member 40. Similarly, the second pressure applicator plate 112 would not then be attached to the second elongate frame member 110 and only contacts the second surface 116b (see FIG. 2) of the second elastomer member 114. Also, the second sensing device circuit board 106, which includes the second pressure sensor IC device 107 is attached to the second elongate frame member 110. The operation during pressure application is identical to that of the first plunger 33 device described in the paragraph.

As illustrated in FIG. 2, an electrical calibration device 98 receives the electrical pressure signal from the electrical output, indicated at 96, of the pressure sensor device 64. If required, the calibration device 98 generates a magnitude scaled (amplification or attenuation) version of the electrical pressure signal. The electrical pressure signal is scaled during the calibration process of the tonometer device 11. This is to ensure that the specific applied pressure measured by the pressure sensor device 64 correspond with the actual intraocular pressure within the eye. For this reason calibration is done against more sophisticated clinical tonometer devices such as the Goldmann applanation tonometer.

The first sensing device 60 also comprises a first analog-to-digital converter 102 having an electrical input and an electrical output. The analog-to-digital converter 102 receives the scaled electrical pressure signal at its electrical input, as indicated by 96, and converts this signal to a first digitized pressure signal (DP1) at its electrical output, as indicated by 103. The first digitized pressure signal (DP1) generated at the analog-to-digital convertor output 103 is received at the electrical process controller 16 by means of conductor 58 (see FIG. 1).

As shown in FIG. 2, depending on the number of pressure applicator devices used in the tonometer, each pressure applicator incorporates a sensing device for measuring the applanation pressure applied by its corresponding plunger member.

As shown in FIG. 1, a second sensing device 105 has a sensor input and output, wherein the sensor input receives a pressure magnitude in proportion to the pressure magnitude applied by the second plunger 34 to the eyelid 41. Based on the pressure magnitude received at the sensor input, the sensing device 105 generates a second electrical pressure signal at the sensor output. The electrical pressure signal is sent by means of conductor 101 to the electrical process controller 16 for processing.

As illustrated in FIGS. 1 and 2, the second sensing device 105 comprising a second pressure sensor IC device 107 and a second elastomer interface member 114 having first and second opposing surfaces, as defined by 116a and 116b, respectively (see FIG. 2). The second pressure sensor IC device 107 also includes a pressure sensing surface and an electrical sensor output 115 (FIG. 2). The first surface 116a of the elastomer member 114 is in contact with the pressure sensing surface of the pressure sensor device 107. A second pressure applanation plate 112, which forms part of the second elongate frame member 110, is in contact with the second surface, defined by 116b, of the elastomer interface member 114 As the actuator device 74 (FIG. 1) displaces the pressure applicator plate 112, the elongate frame member 110 and a second contact rod 122 outwards, as indicated by arrow F2, the pressure applicator plate 112 applies a specific displacement to the second surface 116b of the elastomer interface member 114. This displacement generates a corresponding pressure within the elastomer interface 114, which in turn is applied to the second surface 116b. As the first surface, defined by 116a, of the elastomer interface 114 is compressed against the surface of the pressure sensor IC 107, the sensor output of the second pressure sensor IC 107 generates a corresponding electrical pressure signal, which is in proportion to the specific applanation pressure applied by the elastomer interface to its pressure sensing surface.

Referring to FIG. 2, a second electrical calibration device 118 receives the electrical pressure signal from the electrical output 115 of the pressure sensor device 107. If required, the calibration device 98 generates a magnitude scaled (amplification or attenuation) version of the electrical pressure signal. The electrical pressure signal is scaled during the calibration process of the tonometer device 11. This is to ensure that the specific applied pressure measured by the second pressure sensor device 107 corresponds with the actual intraocular pressure within the eye. For this reason calibration is done against more sophisticated clinical tonometer devices such as the Goldmann applanation tonometer.

The second sensing device 105 also comprises a second analog-to-digital converter 123 having an electrical input and an electrical output. The second analog-to-digital converter 123 receives the scaled electrical pressure signal at its electrical input, as indicated by 120, and converts this signal to a second digitized pressure signal (DP2) at its output, as indicated by 126. The second digitized pressure signal (DP2) generated at the output 126 is received at the electrical process controller 16 by means of conductor 101 (see FIG. 1).

Figure 3:
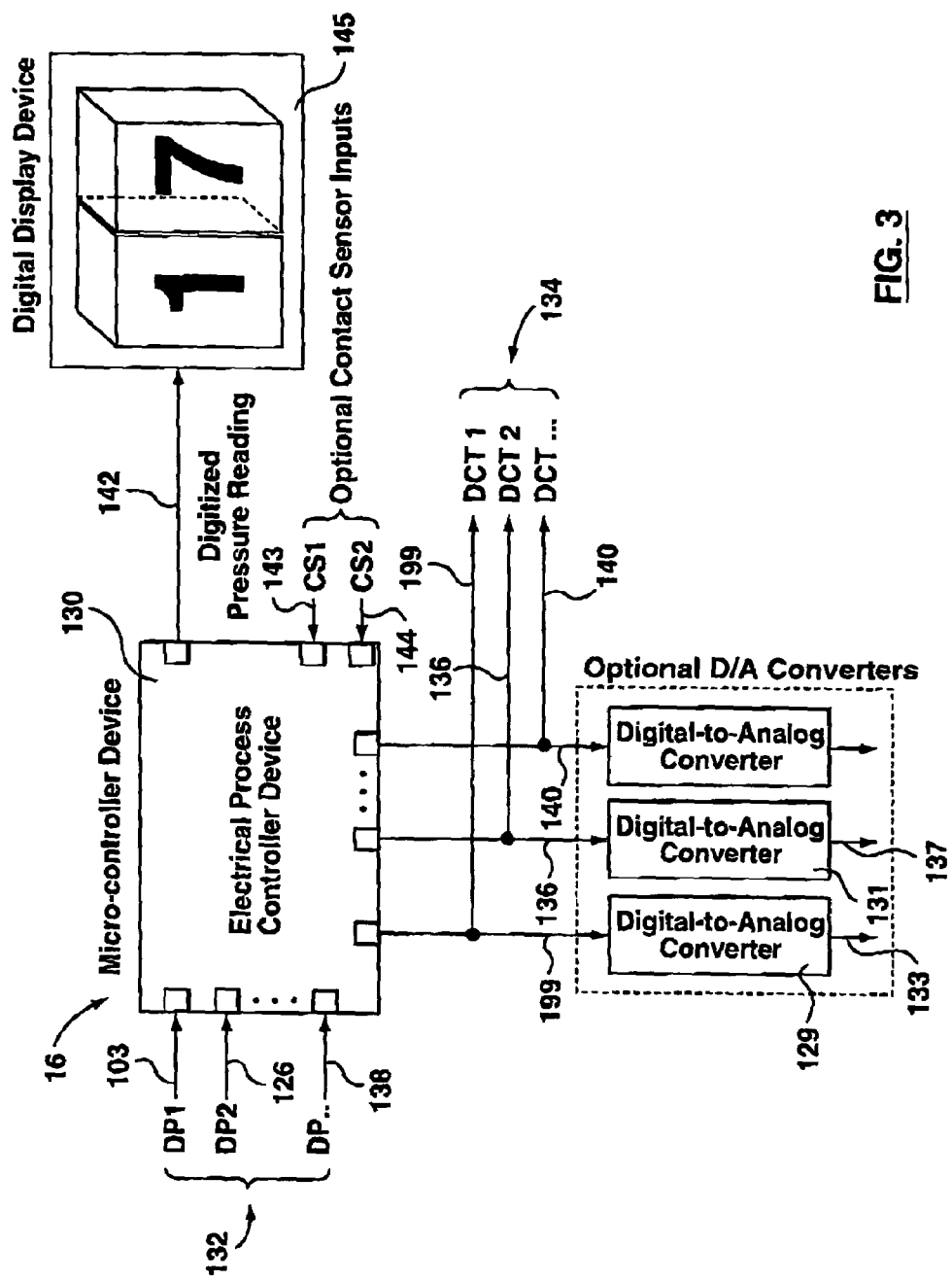
FIG. 3 illustrates a block diagram representation of an electrical process controller incorporated within a tonometer device shown in FIG. 1.

As illustrated in FIG. 3, the electrical process controller 16 comprises a firmware programmed microcontroller 130 (e.g. Philips 87LPC762), which includes on-chip memory for storing calibrated digital pressure values based on the calibration of the tonometer device 11. The electrical process controller 16 maps the received first and second digitized pressure signals (corresponds to the applied applanation pressure by the first and second plunger 33, 34) to the stored calibrated digital pressure values in memory. The retrieved calibrated digital pressure values are used in subsequent processing steps (detailed in the following paragraphs) for determining the intraocular pressure within the eye.

The microcontroller 130 comprises a plurality of digital pressure inputs 132 for receiving digitized pressure signals from the each sensing device, such as sensing devices 60 and 105. If the tonometer 11 is implemented with more than two plunger members, additional sensing devices, such as sensing device 128 (shown in FIG. 2) will be added. For each added plunger member, additional sensing devices are required. As a consequence, more digital pressure inputs are then required at the microcontroller 130.

The microcontroller 130 also comprises a plurality of digital control outputs 134 for controlling the actuation of each of the plunger members. Based on the received first digitized pressure signal (DP1), indicated at 103, the microcontroller 130 generates a first digital control signal, as indicated at 128, which actuates the first plunger member accordingly. Similarly, based on the received second digitized pressure signals (DP2), indicated at 126, the microcontroller 130 generates a second digital control signal, as indicated at 136, which actuates the second plunger member. An additional digital pressure input, as indicated by 138, and the additional digital control output, as indicated by 140, can be utilized if the tonometer 11 includes a third plunger member.

Referring to FIGS. 1 and 3, it will be appreciated that in accordance with the present invention, the first and second actuator devices 68, 74 may both include a DC motor device, which is directly controlled by means of the electrical process controller 16. In this embodiment, a first digital-to-analog convertor 129 converts the digital control output, defined by 128, generated by the electrical process controller 16 into a first DC analog control signal, indicated at 133, that drives a first DC motor. Similarly, a second digital-to-analog convertor 131 converts the digital control output, indicated at 136, generated by the electrical process controller 16 into a second analog DC control signal 137 that drives a second DC motor. Both analog DC control signals 133, 137 may require suitable amplification prior to driving the DC motors.

As previously mentioned, the tonometer can be adapted to use multiple plunger members, wherein each plunger member has a corresponding transducer device. Each transducer device sends and receives pressure and control information from the microcontroller 130 in order to actuate its corresponding plunger member to provide applanation pressure to the subject's eye. Each plunger member provides applanation pressure to a specific region of the eye during the measurement of intraocular pressure. The microcontroller 130 also includes a digital reading output, as indicated by 142. Once the microcontroller 130 determines the magnitude of intraocular pressure, it generates a digitized pressure reading corresponding to intraocular pressure at the digital reading output, indicated by 142. A digital display device 145 receives the digitized pressure reading from the digital reading output, indicated by 142, and displays the digitized pressure reading corresponding to intraocular pressure.

It will be appreciated that in accordance with the present invention, the electrical process controller 16 can also be implemented using known FPGA devices or as a custom fabricated ASIC (application specific IC).

Figure 4:
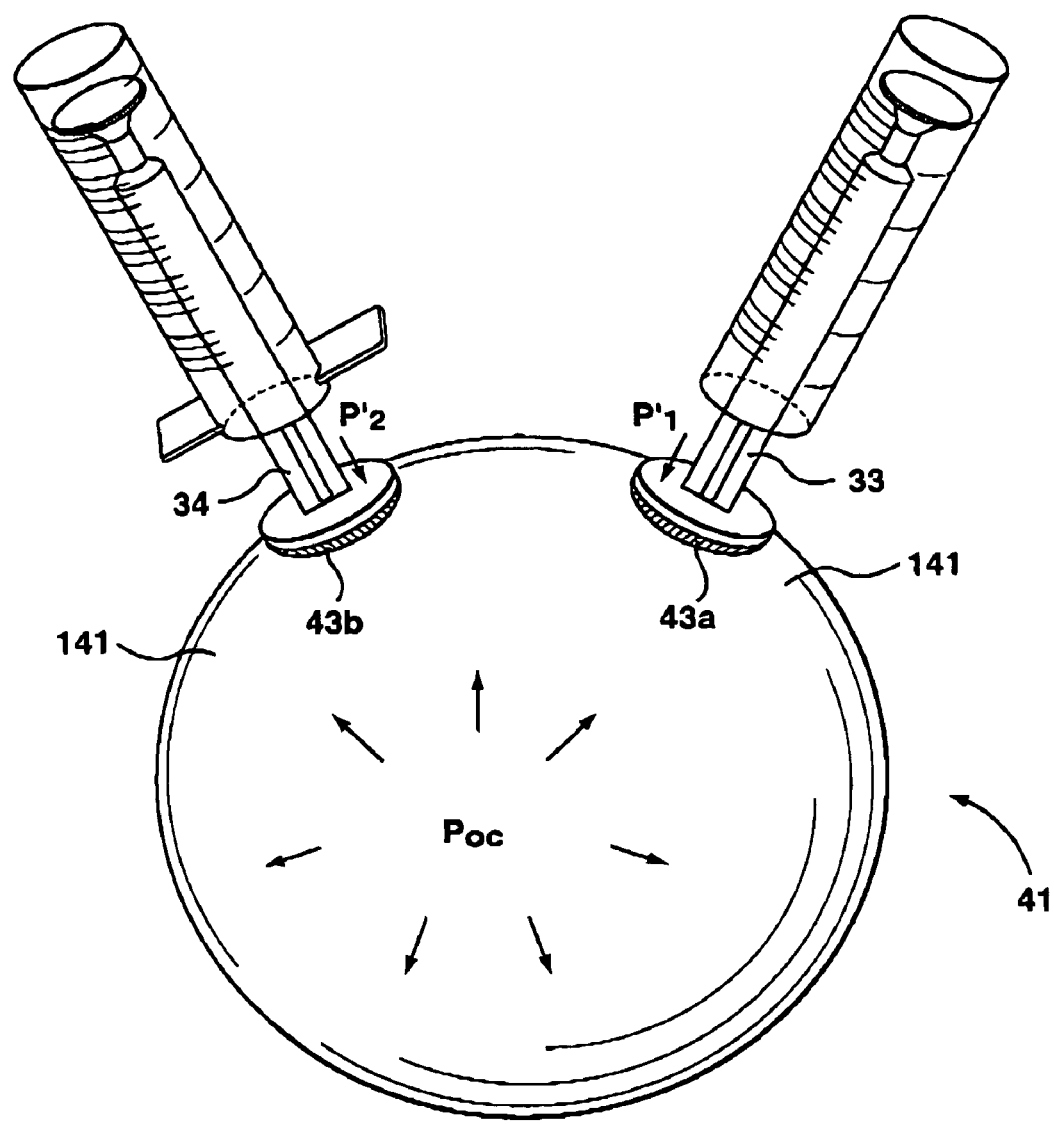
FIG. 4 illustrates the operating principle of the tonometry system shown in FIG. 1.

As illustrated In FIG. 4, in use, the first plunger member 33 applies a constant known reference pressure, defined by P'1, to a first location on the surface of the patient or subject's eyelid, as defined by 43a. The constant reference pressure i s maintained on the eyelid 41, whilst the second plunger 34 applies a steadily increasing second pressure, defined by P'2, to a second location on the subject's eyelid 43b.

The steadily increasing second pressure is applied to a second location on the subject's eyelid, as defined by 43b, until a slight increase in the known reference pressure is detected at the first location on the subject's eyelid 43a. During this step, the position of the first plunger 33 is maintained fixed. When the slight increase in the known reference pressure is detected, the application of the steadily increasing second pressure to the second location of the eyelid 43b is terminated. The increase in known reference pressure as a result of the steadily increasing second pressure, signifies the point at which the combined effect of the second applied pressure and intraocular pressure, defined by $P_{oc}$, within the eyeball just about overcome the applied known reference pressure. Therefore, the intraocular pressure is determined from the known reference pressure and the second pressure at the instant its steady increase is terminated.

As previously mentioned, the microcontroller device 130 (illustrated in FIG. 3) is responsible for controlling the actuation of the plunger members and carrying out the required processing steps in order to determine the intraocular pressure magnitude.

It will be appreciated that in accordance with the present invention, pressure is applied to a first location on the eyeball through the application of pressure to the first surface on the eyelid 43a. Similarly, pressure is applied to a second location of the eyeball through the application of pressure through the second surface on the yelid 43b.

Figure 5:
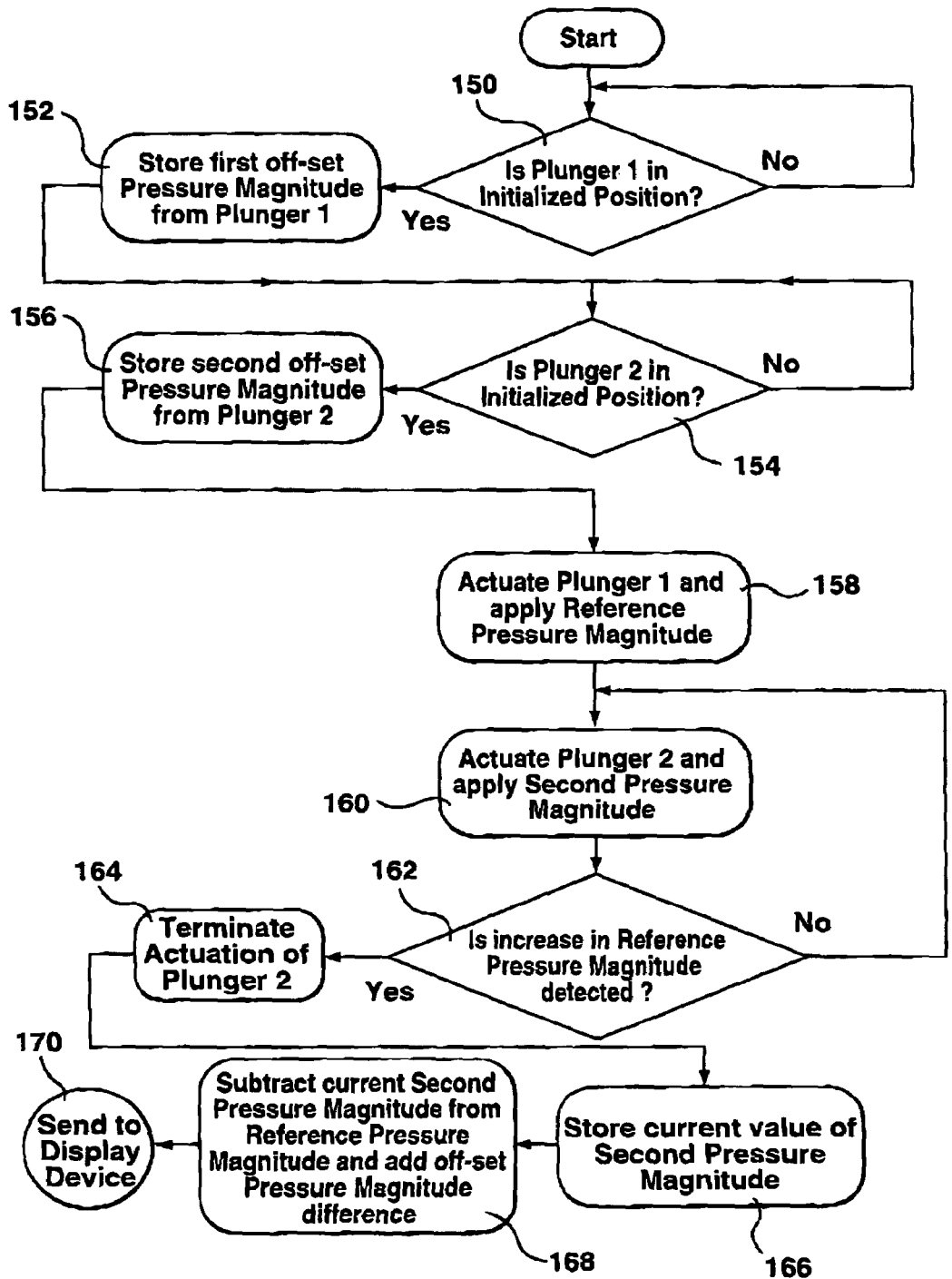
FIG. 5 illustrates a flow chart for the operation of a microcontroller incorporated within the electrical process controller of the tonometer device.

FIG. 5 illustrates a flow diagram representation of the functional processing carried out by the microcontroller device 130. In a step 150, the position of the first contact member 40 relative to the subject's eyelid 41 is monitored in order to ensure that it is in light contact (negligible applied pressure) with the eyelid. This is an initialized position for the first plunger 33. Referring to FIGS. 1 and 3, the initialization position is achieved by the microcontroller 130 actuating plunger member 33 so it is in light contact with the eyelid 41. A contact sensor (not shown) incorporated into contact member 33 generates a first electrical signal, as indicated by 143, which is activated as a result of light contact with the patient or subjects eyelid 41. Once the contact sensor is activated, the generated electrical signal, as indicated by 143, is received and processed by the microcontroller 130, wherein the microcontroller 130 terminates actuation of the plunger member 33.

Referring to FIG. 1, in achieving the initialized position, the first plunger 33 can also be manually adjusted by the patient. A first manual adjustment mechanism 84 provides the means for manually adjusting the first plunger member 33 in order to achieve the initialized position. The manual adjustment mechanism 84 provides axial movement for the first elongate member 54 and therefore the first plunger member 33 connected to it. The manual adjustment mechanism 84 is screw threaded into the outer casing 24 of the right hand end of the housing, defined by 88.

As the adjustment mechanism 84 is turned clockwise, it engages the right hand end portion of the first elongate member 54, as defined by 90. Continued clockwise adjustment of the adjustment mechanism 84 pushes the elongate member 54 and first plunger 33 in the direction of the patients eye until light contact (negligible applanation pressure) is made with the eyelid 41. The contact sensor or switch (not shown in FIG. 1) incorporated within the first contact member generates an audible signal such as beep for indicating that the first plunger member is in light contact with the eyelid and has been initialized. At this point, adjustment of the manual adjustment mechanism is stopped.

Once the first plunger 33 is in the initialized position (achieved manually or by the microprocessor in step 150), a first initialization pressure signal is generated by the pressure sensor device 64. The first initialization pressure signal occurs as result of the first applanation plate 69 compressing the elastomer member 66 during the clockwise adjustment of the manual adjustment mechanism 84. The first initialization pressure signal is converted to a first electrical off-set pressure magnitude by means of the first sensor device 64 and the analog-to-digital convertor 102 (FIG. 2). In a step 152, the electrical off-set pressure magnitude is stored by the microcontroller 130 (FIG. 3) and used in subsequent calculations of intraocular pressure magnitude.

In a step 154, the position of the second contact member 42 relative to the subject's eyelid is monitored in order to ensure that it is also in light contact with the eyelid 41. This is an initialized position for the second plunger member 34. Referring to FIGS. 1 and 3, the initialization position is achieved by the microcontroller 130 actuating second plunger member 34 so it is in light contact with the eyelid 41. A contact sensor (not shown) incorporated into contact member 34 generates a second electrical signal, as indicated by 144, which is activated as a result of light contact with the patient or subjects eyelid 41. Once the contact sensor is activated, the generated electrical signal, as indicated by 144, is received and processed by the microcontroller 130, wherein the microcontroller 130 terminates actuation of the second plunger member 34.

Referring to FIG. 1, in achieving the initialized position, the second plunger 34 can also be manually adjusted by the patient. A second manual adjustment mechanism 85 provides the means for manually adjusting the second plunger member 34 and achieving the initialized position. The manual adjustment mechanism 85 provides axial movement for the second elongate member 110 and therefore the second plunger member 34 connected to it. As with the first manual adjustment mechanism 84, the second manual adjustment mechanism 85 is also screw threaded into the outer casing 24 of the right hand end of the housing 22.

As the second adjustment mechanism 85 is turned clockwise, it engages the right hand end portion of the second elongate member 110. Continued clockwise adjustment of the second adjustment mechanism 85 pushes the second elongate member 110 and second plunger 34 in the direction of the patient's eye until light contact (negligible applanation pressure) is made with the eyelid 41. A contact sensor or switch (not shown in FIG. 1) incorporated within the second contact member 42 generates an audible signal such as beep for indicating that the second plunger member is in light contact with the eyelid 41 and has been initialized.

Once the second plunger 34 is in the initialized position (achieved manually or by the microprocessor in step 154), a second initialization pressure signal is generated by the pressure sensor device 105. The second initialization pressure value occurs as result of the second applanation plate 112 compressing the second elastomer member 114 during the clockwise adjustment of the second manual adjustment mechanism 85. The second initialization pressure signal is converted to a second electrical off-set pressure magnitude by means of the second pressure sensor 107 and the second analog-to-digital convertor 123 (FIG. 2).

In a step 156, the second electrical off-set pressure magnitude is stored by the microcontroller 130 (FIG. 3) and used in subsequent calculations of intraocular pressure magnitude.

During adjustment of both the first and second manual adjustment mechanisms 84, 85, the first and second applanation plates 69, 112 disengage from the first and second contact rods 82, 122, respectively. Accordingly, the microprocessor 130 initiates an automated response by actuating the first and second contact rods 82, 122, such that they engage the first and second applanation plates 69, 112. In essence, the contact rods 82, 122 are catching up with the displaced applanation plates 69, 112 once the plungers 33, 34 and elongate members 54, 110 are in the initialized positions. As the contact rods 82, 122 engage the applanation plates 69, 112, any additional pressure applied by the contact rods 82, 122 will cause the applanation plates to further compress each elastomer member 66, 114. This will in turn cause the pressure sensors 64, 107 and analog-to-digital convertor devices 102, 123 to generate higher pressure magnitudes than the stored first and second off-set pressure magnitudes determined in steps 152 and 156 (FIG. 5). The microcontroller 130 then responds by actuating the motor devices 76, 77 (FIG. 1) in order to reverse (back-off) the position of the contact rods 82, 122, until the pressure sensors 64, 107 and analog-to-digital convertor devices 102, 123 generate the same pressure magnitudes as the previously stored first and second off-set pressure magnitudes. The tonometry system 10 is now both mechanically and electrically initialized.

In a step 158, the microcontroller device actuates the first plunger member 33 in order to apply a constant known reference pressure to a first location on the subject's eyelid, which causes applanation of the eyeball. The first pressure sensor 64 and first analog-to-digital convertor 102 convert the constant known reference pressure to a corresponding reference pressure magnitude. The reference pressure magnitude is received by the first digitized pressure input 103 (FIG. 3) of the microcontroller 130 and stored for processing. As the first plunger 33 resumes the application of the constant known reference pressure to the eyelid (step 168), in a step 160, the microcontroller actuates the second plunger member 34 to apply a steadily increasing second applanation pressure to a second location on the subject's eyelid.

In a step 162, the microcontroller continuously monitors the reference pressure magnitude, whilst continuing to increase the second applanation pressure by actuating the second plunger 34. Once a slight increase in the reference pressure magnitude is detected by the microcontroller, in a step 164, the microcontroller terminates the actuation of the second plunger 34.

The second pressure sensor 107 and second analog-to-digital convertor 123 generate an electrical second pressure magnitude, which corresponds to the increasing second applanation pressure applied by the second plunger 34. The second pressure magnitude is received by the second digitized pressure input 126 (FIG. 3) of the microcontroller. In a step 166, the microcontroller stores the second pressure magnitude applied by the second plunger 34 to the eyelid, once the actuation of the plunger 34 is terminated, as defined in step 164.

The first off-set pressure magnitude, the second off-set pressure magnitude, the reference pressure magnitude and the second pressure magnitude obtained from steps 152, 156, 158 and 166 respectively, are processed in a step 168 by the microcontroller. In the step 168, the microcontroller determines the difference between the first and second off-set pressure magnitudes. Both the first and second off-set pressure magnitudes must be measured to be approximately the same, following the initializing of the plunger members (steps 150 and 154). However, in use, differences in component tolerances (in the sensing member) and the differences in the off-set pressure magnitudes as a result of the manual adjustment process, require the accountability of the off-set pressure magnitudes in the calculation of intraocular pressure. Once the difference between the first and second off-set pressure magnitudes have been generated, the microcontroller calculates a pressure magnitude from the second pressure magnitude and from the reference pressure magnitude.

In a step 170, the calculated pressure magnitude is sent to the digital reading output, as defined by 142 (FIG. 3) of the microprocessor 130. The digital display device 145 (FIG. 3) receives and displays the calculated pressure magnitude corresponding to intraocular pressure within the eye.

As shown in FIG. 1, the hands free holder 12 comprises a cylindrical body 175 and fastening means 180a, 180b. In use, the hands free holder's fastening means 180a, 180b secure to wedged shaped grooves 186a, 185b located on the main body 20 of the tonometer 11. Once the hands free holder 12 is secured to the tonometer 11, it can be strapped around the back of the subject or patients head using elasticated adjustable straps 188a, 188b in order to place the tonometer device 11 over the eye. For this reason the left hand end portion of the cylindrical body 175 includes a pair of oval contact pads 190a, 190b for contacting above and below the eye.

Figure 6:
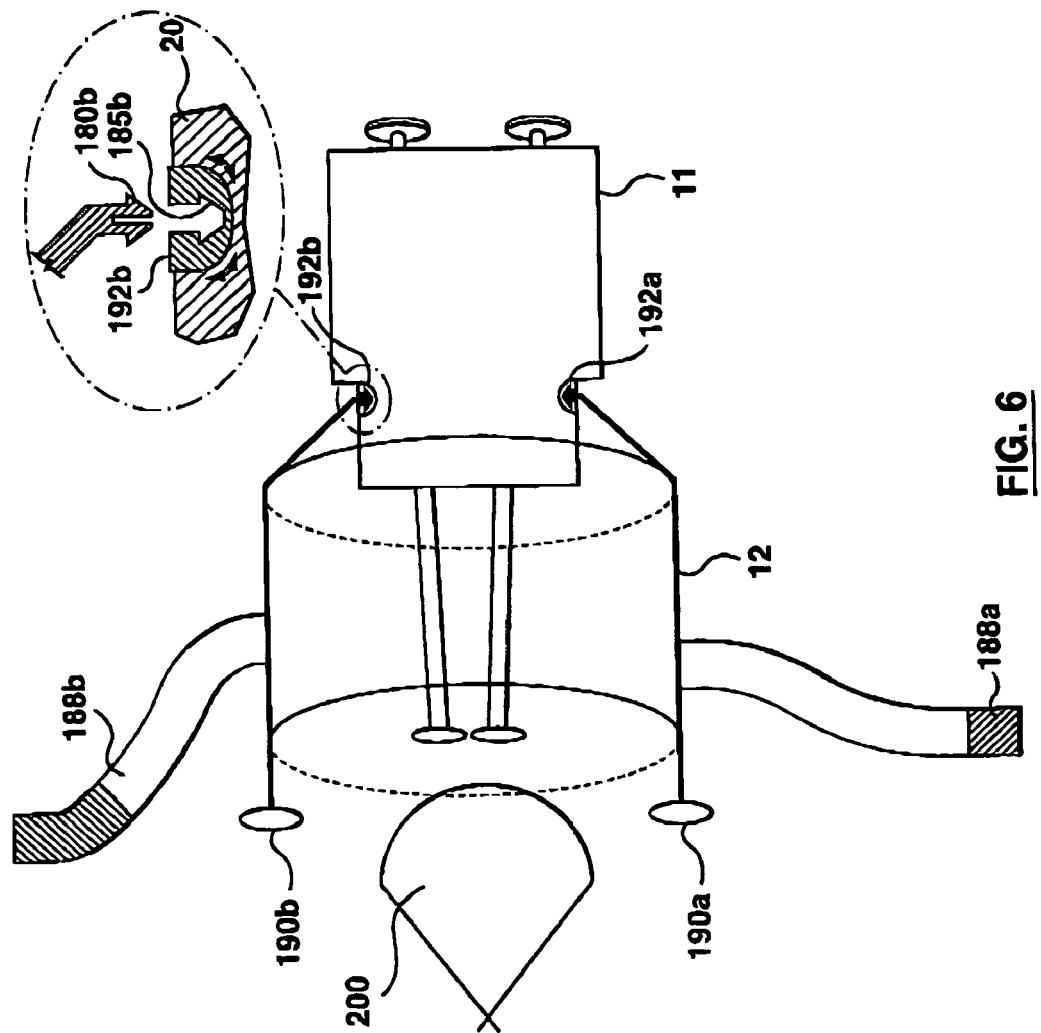
FIG. 6 illustrates a hands free holder for securing the tonometer device over a patient's eye, whilst the tonometer device is in use.

As illustrated in FIG. 6, the oval contact pads 190a, 190b are positioned above and below the eye 200 and the straps 188a, 188b are secured around the back of the patient's head. The elasticated nature of the straps 188a, 188b secures the hands free holder 12 and tonometer 11 in a relatively perpendicular orientation to the patient's facial profile. Once the hands free holder 12 and tonometer 11 are secured, the tonometer 11 can be angularly adjusted relative to the eyelid by means of a pair of adjustment bearings 192a, 192b mounted within the main body of the tonometer 11. A wedged shaped groove 185a is provided within each adjustment bearing 192a, 192b. By applying a tilting force (in any given direction) to the right hand end portion of the tonometer 11, the adjustment bearings 192a, 192b slide within the their mounted positions within the main body 20.

It is desirable to record diurnal (occurring in a 24-hour period) variations in intraocular pressure overnight. It has been found that glaucoma patients have much higher diurnal intraocular pressure variations (8–11 mm Hg) In comparison to healthy subjects (about 4 mm Hg variations). The Firmware in the microcontroller enables the tonometer device to make automated measurements whilst the patient is sleeping, which enables the measurement of diurnal variations in intraocular pressure overnight.

The embodiment of the present invention provides an applanation tonometry system with integrated electrical processing circuitry for calculating intraocular pressure and variations in intraocular pressure. It should be understood that various modifications can be made to the preferred and alternative embodiments described and illustrated herein, the scope of which is defined in the appended claims.

I claim:

1. A method of obtaining pressure within the eyeball of a subject, the method comprising the steps of:
   (a) applying a constant known first reference pressure to a first location on the eyelid of the subject, wherein applying the constant known reference pressure to the first location on the eyelid comprises pressing a first applanation disk to the first location on the eyelid;
   (b) applying at least a second pressure to an at least second location on the eyelid of the subject, applying the second pressure to the second location on the eyelid comprises pressing a second applanation disk to the second location on the eyelid;
   (c) increasing the second pressure until a slight increase in the pressure is detected at the first location beyond the constant known reference pressure; and
   (d) noting the second pressure being applied at the time the increase in the pressure is detected at the first location, the noted second pressure being an indication of the pressure within the eyeball.

2. A method as claimed in claim 1, which includes the step of calculating intraocular pressure from the noted second pressure and the first reference pressure.

3. A method as claimed in claim 2, which includes the step of converting the calculated intraocular pressure into an electrical signal.

4. A method as claimed in claim 3, which includes providing a display device, for applying the electrical signal to the display device, for displaying of a reading indicative of pressure within the eyeball.

5. A method as claimed in claim 1, which includes applying more than one second pressure to the eyelid, each said second pressure being applied at a separate second location on the eyelid.

6. A method as claimed in claim 1, which includes the step of calculating intraocular pressure as being generally equal to the difference between the noted second pressure and the first reference pressure.

* * * * *